(12) United States Patent
Gellman

(10) Patent No.: US 7,112,226 B2
(45) Date of Patent: *Sep. 26, 2006

(54) MALE URETHRAL STENT DEVICE

(75) Inventor: Barry Gellman, Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 100 days.

This patent is subject to a terminal disclaimer.

(21) Appl. No.: 10/811,196

(22) Filed: Mar. 26, 2004

(65) Prior Publication Data

US 2004/0181287 A1 Sep. 16, 2004

Related U.S. Application Data

(63) Continuation of application No. 10/277,575, filed on Oct. 22, 2002, now Pat. No. 6,733,536.

(51) Int. Cl.
A61F 2/04 (2006.01)
A61F 2/02 (2006.01)
A61M 5/00 (2006.01)

(52) U.S. Cl. ............... 623/23.66; 604/8; 623/23.7; 623/23.75; 623/23.69

(58) Field of Classification Search ............ 623/23.66, 623/23.69, 23.7, 1.12, 1.15, 23.75; 604/8; 606/108, 198

See application file for complete search history.

(56) References Cited

U.S. PATENT DOCUMENTS

| 3,527,226 | A | 9/1970 | Hakim et al. |
| 3,657,744 | A | 4/1972 | Ersek |
| 3,923,066 | A | 12/1975 | Francisoud et al. |
| 3,938,529 | A | 2/1976 | Gibbons |
| 4,154,242 | A | 5/1979 | Termanini |
| 4,156,067 | A | 5/1979 | Gould |
| 4,240,434 | A | 12/1980 | Newkirk |
| 4,307,723 | A | 12/1981 | Finney |
| 4,423,725 | A | 1/1984 | Baran et al. |
| 4,627,838 | A | 12/1986 | Cross et al. |
| 4,655,771 | A | 4/1987 | Wallsten |
| 4,660,560 | A | 4/1987 | Klein |

(Continued)

FOREIGN PATENT DOCUMENTS

EP 0 274 846 7/1988

(Continued)

OTHER PUBLICATIONS

Duerig et al.; "An Overview of Superelastic Stent Design"; © 2000 Isis Medical Media Ltd.; (pp. 235-246).

(Continued)

Primary Examiner—Corrine McDermott
Assistant Examiner—Thomas J. Sweet
(74) Attorney, Agent, or Firm—Edwards Angell Palmer & Dodge LLP

(57) ABSTRACT

A stent for treatment of a body lumen through which a flow is effected on either side of a sphincter, said stent comprising one or more windings and having an inner core substantially covered by an outer core and including a first segment, a second segment, and a connecting member disposed between the segments. When the stent is positioned within a patient's urinary system, the first segment and second segments are located on either side of the external sphincter to inhibit migration of the stent while not interfering with the normal functioning of the sphincter. The outer coating comprises an absorbable material that provides temporary structural support to the stent. After absorption of substantially all the outer coating of the stent, the remaining relatively compliant inner core facilitates easy removal by the patient by pulling a portion of the stent that extends outside the patient's body for this purpose.

17 Claims, 6 Drawing Sheets

U.S. PATENT DOCUMENTS

| | | |
|---|---|---|
| 4,713,049 A | 12/1987 | Carter |
| 4,732,152 A | 3/1988 | Wallsten et al. |
| 4,768,507 A | 9/1988 | Fischell et al. |
| 4,771,773 A | 9/1988 | Kropf |
| 4,813,429 A | 3/1989 | Eshel et al. |
| 4,895,566 A | 1/1990 | Lee |
| 4,931,037 A | 6/1990 | Wetterman |
| 4,932,938 A | 6/1990 | Goldberg et al. |
| 4,954,126 A | 9/1990 | Wallsten |
| 4,955,859 A | 9/1990 | Zilber |
| 4,973,301 A | 11/1990 | Nissenkorn |
| 4,990,155 A | 2/1991 | Wilkoff |
| 4,994,066 A | 2/1991 | Voss |
| 4,995,868 A | 2/1991 | Brazier |
| 5,026,377 A | 6/1991 | Burton et al. |
| 5,037,427 A | 8/1991 | Harada et al. |
| 5,041,092 A | 8/1991 | Barwick |
| 5,059,169 A | 10/1991 | Zilber .......................... 604/8 |
| 5,061,275 A | 10/1991 | Wallsten et al. |
| 5,078,720 A | 1/1992 | Burton et al. |
| 5,087,252 A | 2/1992 | Denard |
| 5,116,309 A | 5/1992 | Coll |
| 5,122,154 A | 6/1992 | Rhodes |
| 5,147,370 A | 9/1992 | McNamara et al. |
| 5,160,341 A | 11/1992 | Brenneman et al. |
| 5,167,614 A | 12/1992 | Tessmann et al. |
| 5,176,625 A | 1/1993 | Brisson |
| 5,176,626 A | 1/1993 | Soehendra |
| 5,183,085 A | 2/1993 | Timmermans |
| 5,195,989 A | 3/1993 | Euteneuer |
| 5,217,451 A | 6/1993 | Freitas |
| 5,220,927 A | 6/1993 | Astrahan et al. |
| 5,222,971 A | 6/1993 | Willard et al. |
| 5,224,953 A | 7/1993 | Morgentaler |
| 5,234,456 A | 8/1993 | Silvestrini |
| 5,246,445 A | 9/1993 | Yachia et al. ................ 605/108 |
| 5,258,020 A | 11/1993 | Froix |
| 5,269,802 A | 12/1993 | Garber |
| 5,282,784 A | 2/1994 | Willard |
| 5,282,823 A | 2/1994 | Schwartz et al. |
| 5,286,254 A | 2/1994 | Shapland et al. |
| 5,292,315 A | 3/1994 | Euteneuer |
| 5,300,022 A | 4/1994 | Klapper et al. |
| 5,304,121 A | 4/1994 | Sahatjian |
| 5,316,016 A | 5/1994 | Adams et al. |
| 5,322,501 A | 6/1994 | Mahmud-Durrani |
| 5,342,348 A | 8/1994 | Kaplan |
| 5,344,395 A | 9/1994 | Whalen et al. |
| 5,352,198 A | 10/1994 | Goldenberg et al. |
| 5,354,263 A | 10/1994 | Coll |
| 5,354,309 A | 10/1994 | Schnepp-Pesch et al. ... 606/198 |
| 5,356,423 A | 10/1994 | Tihon et al. |
| 5,364,340 A | 11/1994 | Coll |
| 5,372,600 A | 12/1994 | Beyar et al. |
| 5,383,928 A | 1/1995 | Scott et al. ...................... 623/1 |
| 5,391,196 A | 2/1995 | Devonec |
| 5,409,460 A | 4/1995 | Krumme |
| 5,419,760 A | 5/1995 | Narciso, Jr. |
| 5,421,955 A | 6/1995 | Lau et al. |
| 5,429,634 A | 7/1995 | Narciso, Jr. |
| 5,441,515 A | 8/1995 | Khosravi et al. |
| 5,441,516 A | 8/1995 | Wang et al. |
| 5,456,667 A | 10/1995 | Ham et al. |
| 5,464,650 A | 11/1995 | Berg et al. |
| 5,496,277 A | 3/1996 | Termin et al. |
| 5,499,994 A | 3/1996 | Tihon et al. |
| 5,514,176 A | 5/1996 | Bosley, Jr. |
| 5,514,178 A | 5/1996 | Torchio ......................... 623/12 |
| 5,514,669 A | 5/1996 | Selman |
| 5,520,697 A | 5/1996 | Lindenberg et al. |
| 5,536,242 A | 7/1996 | Willard et al. |
| 5,540,701 A | 7/1996 | Sharkey et al. ............. 606/153 |
| 5,540,713 A | 7/1996 | Schnepp-Pesch et al. ... 606/198 |
| 5,545,208 A | 8/1996 | Wolff et al. |
| 5,545,211 A | 8/1996 | An et al. |
| 5,549,559 A | 8/1996 | Eshel |
| 5,549,595 A | 8/1996 | Freitas |
| 5,554,181 A | 9/1996 | Das |
| 5,556,413 A | 9/1996 | Lam |
| 5,562,622 A | 10/1996 | Tihon |
| 5,584,872 A | 12/1996 | LaFontaine et al. |
| 5,588,965 A | 12/1996 | Burton et al. |
| 5,593,403 A | 1/1997 | Buscemi |
| 5,599,306 A | 2/1997 | Klein et al. |
| 5,601,591 A | 2/1997 | Edwards et al. |
| 5,609,583 A | 3/1997 | Hakki et al. |
| 5,609,629 A | 3/1997 | Fearnot et al. |
| 5,618,299 A | 4/1997 | Khosravi et al. |
| 5,626,562 A | 5/1997 | Castro |
| 5,653,684 A | 8/1997 | Laptewicz |
| 5,667,486 A | 9/1997 | Mikulich et al. |
| 5,667,490 A | 9/1997 | Keith et al. |
| 5,674,241 A | 10/1997 | Bley et al. |
| 5,676,693 A | 10/1997 | LaFontaine |
| 5,702,361 A | 12/1997 | Evans et al. |
| 5,702,419 A | 12/1997 | Berry et al. |
| 5,707,386 A | 1/1998 | Schnepp-Pesch et al. ... 606/194 |
| 5,723,003 A | 3/1998 | Winston et al. |
| 5,725,549 A | 3/1998 | Lam |
| 5,733,303 A | 3/1998 | Israel et al. |
| 5,738,654 A | 4/1998 | Tihon |
| 5,766,209 A | 6/1998 | Devonec ......................... 604/8 |
| 5,766,238 A | 6/1998 | Lau et al. |
| 5,772,668 A | 6/1998 | Summers et al. |
| 5,776,142 A | 7/1998 | Gunderson |
| 5,776,161 A | 7/1998 | Globerman |
| 5,782,838 A | 7/1998 | Beyar et al. |
| 5,792,400 A | 8/1998 | Talja et al. |
| 5,797,952 A | 8/1998 | Klein |
| 5,817,102 A | 10/1998 | Johnson et al. |
| 5,824,037 A | 10/1998 | Bogarty et al. |
| 5,824,038 A | 10/1998 | Wall |
| 5,830,179 A | 11/1998 | Mikus et al. |
| 5,833,707 A | 11/1998 | McIntyre et al. |
| 5,843,103 A | 12/1998 | Wulfman |
| 5,865,815 A | 2/1999 | Tihon |
| 5,876,417 A | 3/1999 | Devonec et al. |
| 5,876,445 A | 3/1999 | Andersen et al. |
| 5,888,201 A | 3/1999 | Stinson et al. |
| 5,902,317 A | 5/1999 | Kleshinski et al. |
| 5,902,328 A | 5/1999 | LaFontaine et al. |
| 5,911,752 A | 6/1999 | Dustrude et al. |
| 5,916,195 A | 6/1999 | Eshel et al. |
| 5,916,227 A | 6/1999 | Keith et al. |
| 5,928,208 A | 7/1999 | Chu et al. |
| 5,928,217 A | 7/1999 | Mikus et al. |
| 5,938,670 A | 8/1999 | Keith et al. |
| 5,957,929 A | 9/1999 | Brenneman |
| 5,964,732 A | 10/1999 | Willard |
| 5,964,744 A | 10/1999 | Balbierz et al. |
| 5,964,771 A | 10/1999 | Beyar et al. |
| 5,976,165 A | 11/1999 | Ball et al. |
| 5,980,550 A | 11/1999 | Eder et al. |
| 6,001,117 A | 12/1999 | Huxel et al. |
| 6,004,328 A | 12/1999 | Solar |
| 6,017,977 A | 1/2000 | Evans et al. |
| 6,019,779 A | 2/2000 | Thorud et al. |
| 6,022,312 A | 2/2000 | Chaussy et al. |
| 6,023,638 A | 2/2000 | Swanson |
| 6,024,763 A | 2/2000 | Lenker et al. |
| 6,033,413 A | 3/2000 | Mikus et al. |
| 6,042,606 A | 3/2000 | Frantzen |
| 6,047,218 A | 4/2000 | Whayne et al. |
| 6,050,949 A | 4/2000 | White et al. |

| | | |
|---|---|---|
| 6,053,900 A | 4/2000 | Brown et al. |
| 6,066,167 A | 5/2000 | Lau et al. |
| 6,066,168 A | 5/2000 | Lau et al. |
| 6,090,103 A | 7/2000 | Hakky et al. |
| 6,090,115 A | 7/2000 | Beyar et al. |
| 6,113,594 A | 9/2000 | Savage |
| 6,113,597 A | 9/2000 | Eggers et al. |
| 6,119,697 A | 9/2000 | Engel et al. |
| 6,126,667 A | 10/2000 | Barry et al. |
| 6,132,460 A | 10/2000 | Thompson |
| 6,132,461 A | 10/2000 | Thompson |
| 6,139,536 A | 10/2000 | Mikus et al. |
| 6,146,416 A | 11/2000 | Andersen et al. |
| 6,152,919 A | 11/2000 | Hakky |
| 6,156,064 A | 12/2000 | Chouinard |
| 6,162,215 A | 12/2000 | Feng |
| 6,162,231 A | 12/2000 | Mikus et al. |
| 6,165,210 A | 12/2000 | Lau et al. |
| 6,174,305 B1 | 1/2001 | Mikus et al. |
| 6,176,875 B1 | 1/2001 | Lenker et al. |
| 6,179,868 B1 | 1/2001 | Burpee et al. |
| 6,187,015 B1 | 2/2001 | Brenneman |
| 6,214,037 B1 | 4/2001 | Mitchell et al. |
| 6,221,081 B1 | 4/2001 | Mikus et al. |
| 6,238,430 B1 | 5/2001 | Klumb et al. |
| 6,245,103 B1 | 6/2001 | Stinson |
| 6,254,628 B1 | 7/2001 | Wallace et al. |
| 6,258,115 B1 | 7/2001 | Dubrul |
| 6,299,636 B1 | 10/2001 | Schmitt et al. |
| 6,334,866 B1 | 1/2002 | Wall |
| 6,355,061 B1 | 3/2002 | Quiachon et al. |
| 6,355,070 B1 | 3/2002 | Andersen et al. |
| 6,371,979 B1 | 4/2002 | Beyar et al. |
| 6,451,025 B1 | 9/2002 | Jervis |
| 6,494,879 B1 | 12/2002 | Lennox et al. |
| 6,494,908 B1 | 12/2002 | Huxel et al. |
| 6,733,536 B1 * | 5/2004 | Gellman .................. 623/23.66 |
| 2002/0107540 A1 | 8/2002 | Whalen et al. |
| 2002/0177904 A1 | 11/2002 | Huxel et al. |
| 2003/0040803 A1 | 2/2003 | Rioux et al. |
| 2003/0045924 A1 | 3/2003 | Datta et al. |

FOREIGN PATENT DOCUMENTS

| | | |
|---|---|---|
| EP | 0 341 988 | 11/1989 |
| EP | 0 543 309 A1 | 11/1992 |
| EP | 0 935 977 A3 | 8/1999 |
| FR | 2 661 603 | 11/1991 |
| WO | WO 80/01460 | 7/1980 |
| WO | WO 89/03232 | 4/1989 |
| WO | WO 91/16005 | 10/1991 |
| WO | WO 96/23449 | 8/1996 |
| WO | WO 99/23952 | 5/1999 |
| WO | WO 00/15130 | 3/2000 |
| WO | WO 00/16005 | 3/2000 |
| WO | WO 00/18907 | 4/2000 |
| WO | WO 00/19926 | 4/2000 |
| WO | WO 00/21462 | 4/2000 |
| WO | WO 00/45744 | 8/2000 |
| WO | WO 00/51521 | 9/2000 |
| WO | WO 00/56247 | 9/2000 |
| WO | WO 00/59558 | 10/2000 |
| WO | WO 00/69367 | 11/2000 |
| WO | WO 00/69498 | 11/2000 |
| WO | WO 00/76425 | 12/2000 |
| WO | WO 01/10345 | 2/2001 |
| WO | WO 01/56629 | 8/2001 |
| WO | WO 02/05841 | 8/2002 |

OTHER PUBLICATIONS

International Search Report for International Application Ser. No. PCTUS 03/32286, mailing date of Feb. 4, 2004, 4 pages.

* cited by examiner

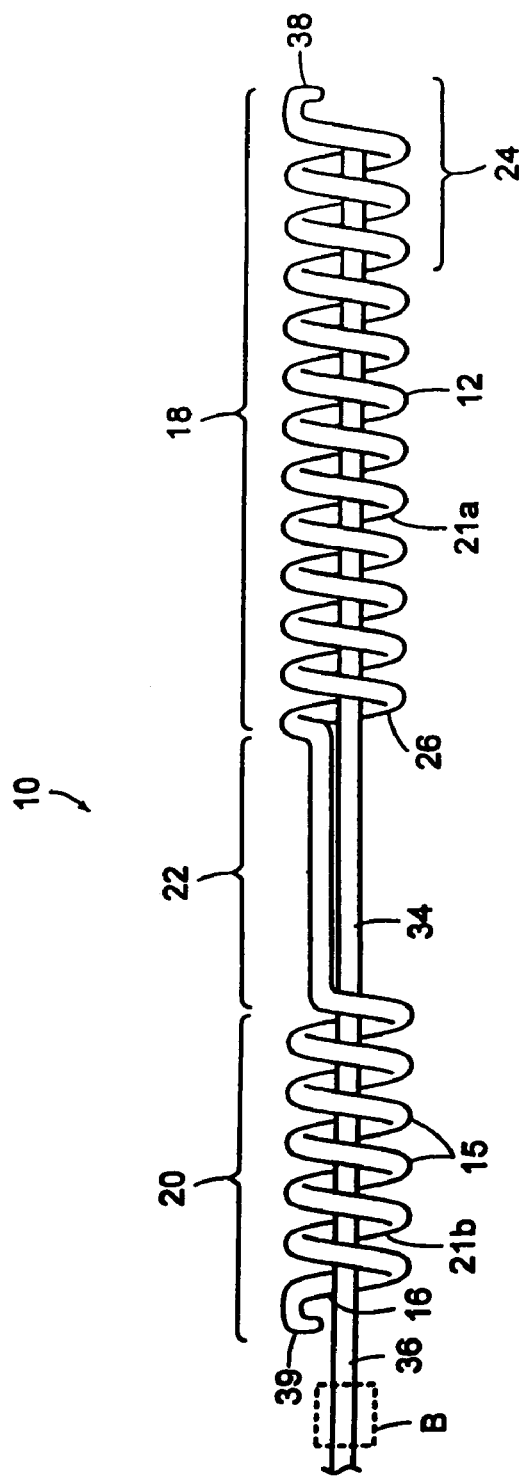
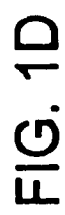
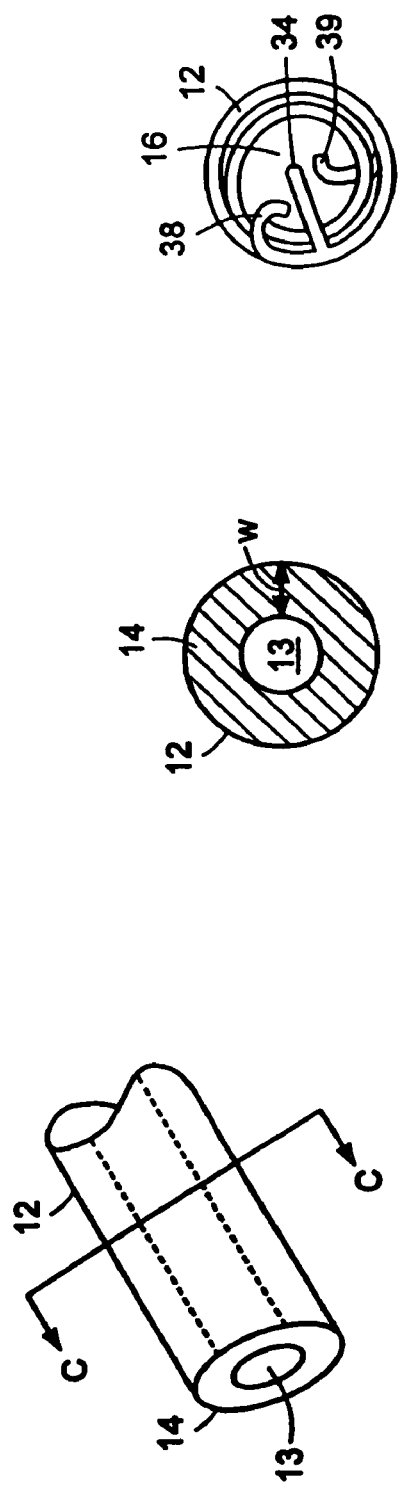
FIG. 1A
FIG. 1B
FIG. 1C
FIG. 1D

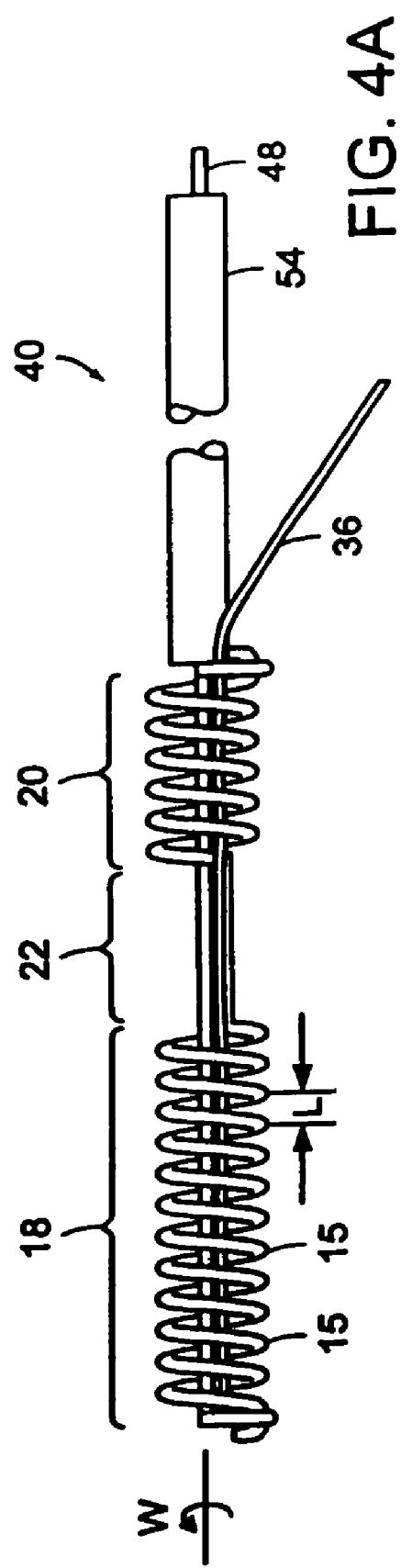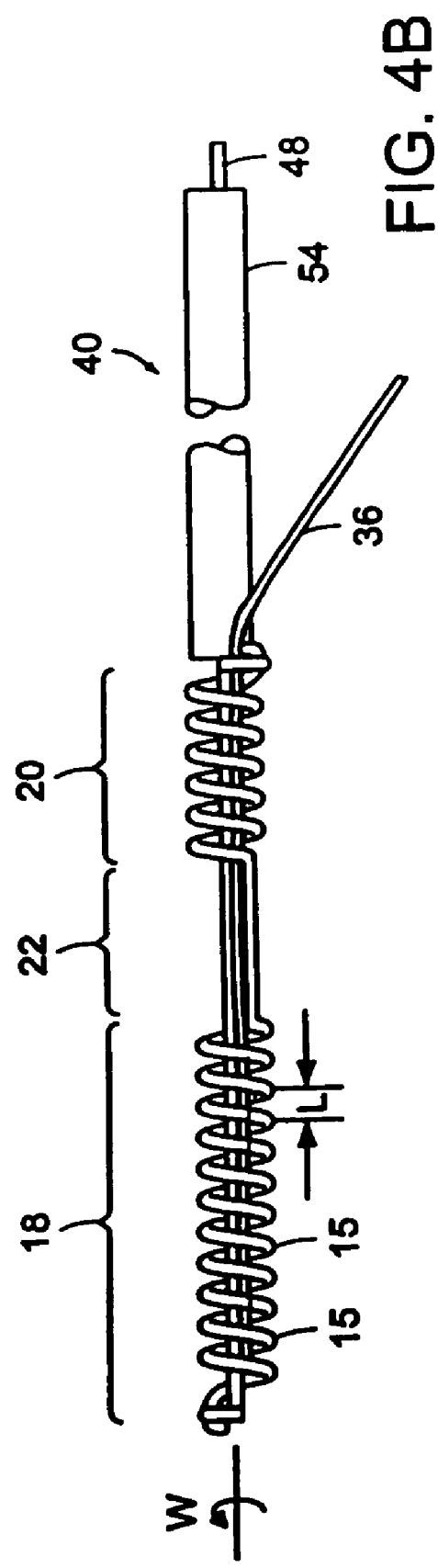
FIG. 4A
FIG. 4B

MALE URETHRAL STENT DEVICE

CROSS-REFERENCE TO RELATED APPLICATIONS

This is a continuation of prior application Ser. No. 10/277,575, filed on Oct. 22, 2002 now U.S. Pat. No. 6,733,536, the entire disclosure of which is incorporated by reference herein.

TECHNICAL FIELD

This invention generally relates to stents and maintaining a body passageway open.

BACKGROUND INFORMATION

Bladder outlet obstruction is a urological disorder. In males, this urological disorder can be caused by an enlarged prostate that constricts the prostatic urethra. Such disorders include, for example, benign prostatic hyperplasia or prostatic carcinoma. The prostatic urethra is a section of the urethra that passes through the prostate. Bladder outlet obstruction is associated with a plurality of undesirable symptoms such as difficulties in urination, strongly reduced capacity to urinate, an increased desire to urinate, or the complete inability to urinate which may lead to severe renal disorders.

To eliminate these symptoms, medical devices that attempt to maintain an open passageway through the prostatic urethra have been developed. One of the medical devices developed for this purpose is a Foley catheter. The Foley catheter is a tube that extends from the patient's bladder to a collection bag located outside of the patient's body. The Foley catheter provides constant drainage, but it does not allow the patient to control his voiding function.

Some indwelling prostatic stents seek to allow the patient to control their voiding function while also retaining the prostatic urethra open. For example, U.S. Pat. No. 5,766,209 describes a prosthesis that contains two tubular elements that are intended to be located on either side of the patient's external sphincter, and a connector that is intended to be held in the orifice of the external sphincter.

Following conclusion of the treatment of the urological disorder (for example, when patency of the urethra is restored), a medical professional is generally required to remove an indwelling prostatic stent either transurethreally or endoscopically. A partially absorbable stent which can be implanted following a surgical procedure and be easily removed by the patient would obviate the need for a patient to return to the doctor for removal of the stent.

SUMMARY OF THE INVENTION

The invention generally relates to draining fluid from the bladder of a patient with a stent. Devices and methods according to the invention are typically used in the treatment for patients suffering from bladder outlet obstruction to address and relieve urinary retention. It is an object of the invention to maintain the urethra open and able to pass fluids from the bladder while also allowing normal operation of the patient's external sphincter such that the patient has control over the retention and discharge of urine (and/or other fluids) from the bladder. It is another object of the invention to resist migration of a device placed within the patient's urinary system, and also to prevent or reduce the attraction of blood clots (and/or other debris) when the device is placed and used within the patient. It is a further object of the invention to permit ease of removal of the device by the patient when patency of the lumen is restored.

It is noted initially that the directional terms proximal and distal require a point of reference. As used herein, the point of reference is from the perspective of the body of the patient. Therefore, the term proximal refers to a direction that points into the body of the patient, whereas the term distal refers to a direction that points out of the patient's body.

In one aspect, the invention features a medical device for use within a body lumen of a patient comprising a first coil, a second coil, and a connecting segment. When placed within the body of the patient the first coil comprises a plurality of windings defining a first lumen and locatable on the proximal side of the external sphincter and a distal end terminating on the proximal side of the external sphincter. The second coil comprises a plurality of windings defining a second lumen and locatable on the distal side of the external sphincter and a proximal end terminating on the distal side of the external sphincter. The connecting segment is locatable in the external sphincter when the device is placed within the body of the patient and is disposed between and couples together the first and second coils. The medical device can have a removal segment attached to a proximal end of the first coil. The removal segment can be disposed within the first lumen and/or the second lumen.

In one embodiment, the first coil, the second coil, and the connecting segment further comprise an inner core and an outer coating covering at least a portion of the inner core. The inner core may be formed from a biocompatible material. In one embodiment, the outer coating is formed from a material that is absorbed into the lumen of a patient at a predetermined degradation rate. The outer coating may be formed from polyglycolic acid, polylactic acid, a polymer, or a polymid. The outer coating may also comprise a pharmaceutical.

In another embodiment, the windings of the first coil and the second coil are sized and configured to progressively uncoil from the proximal end of the first coil to a distal end of the second coil upon application of a continuous tensile force to the removal segment. The proximal end of the first coil may be formed into a variety of shapes to permit atraumatic entry of the medical device into the body of the patient. In one embodiment, the proximal end of the first coil is a frusto-conical shape. In another embodiment, the proximal end of the first coil and the distal end of the second coil include one or more hooks to permit connection to a delivery system.

In one embodiment, the windings of the first coil and the second coil are separated from each other by a distance in the range of from about 0.5 millimeters to about 10 millimeters. In one embodiment, the cross-sectional area of the outer coating is in the range from about 0.0079 millimeters$^2$ to about 7.1 millimeters$^2$.

Another aspect of the invention features a medical device for use within a body lumen of a patient comprising an inner core and an outer coating layered upon a portion of the inner core. The inner core includes a first coil defining a first lumen and having a proximal end and a distal end. The inner core also includes a second coil defining a second lumen having a proximal end and a distal end. The outer coating provides structural support to the first lumen and the second lumen of the inner core when placed with a body lumen of a patient. The inner core further comprises a plurality of spaced coil windings being sized and configured for placement and retention substantially within the urethra of a patient. A connecting segment is disposed between and couples together the first coil and the second coil. In one embodiment, the medical device is of unitary construction. The medical device can also have a removal segment attached to the proximal end of the first coil. The removal segment can be disposed within the first lumen and/or the second lumen.

The inner core may be formed from a biocompatible material. The outer coating may be formed from a material that loses structural integrity during hydration and may be absorbed into the lumen of a patient at a predetermined degradation rate. The outer coating may be formed from polyglycolic acid, polylactic acid, a polymer, or a polymid. The outer coating may also comprise a pharmaceutical.

In another embodiment, the windings are sized and configured to progressively uncoil from the proximal end of the first coil to the distal end of the second coil upon application of a continuous tensile force to the removal segment. The proximal end of the first coil may be formed into a variety of shapes to permit atraumatic entry of the medical device into the body of the patient. In one embodiment, the proximal end of the first coil is a frusto-conical shape. In another embodiment, the proximal end of the first coil and the distal end of the second coil includes one or more hooks to permit connection to a delivery system. In one embodiment, the windings of the first coil and the second coil are separated by a distance in the range of from about 0.5 millimeters to about 10 millimeters. In one embodiment, the cross-sectional area of the outer coating is in the range of from about 0.0079 millimeters$^2$ to about 7.1 millimeters$^2$.

Another aspect of the invention features a method of maintaining the patency of a patient's urethra. The method includes supporting the prostatic section of the urethra with a first coil defining a first lumen and locatable on the proximal side of the external sphincter, supporting the bulbar section of the urethra with a second coil defining a second lumen and locatable on the distal side of the external sphincter, and permitting substantially normal constriction of the external sphincter with a substantially uncoiled segment coupling the first coil and second coil.

The method can include providing a delivery system comprising a first element and a second element. The first element has an outer diameter smaller than the diameters of the first coil and the second coil and includes a first end, a second end, and a connection member extending out from the first end. The second element includes a first end, a second end, and a connection member extending out from the first end with the first and/or the second elements of the delivery system being rotatable. In one embodiment, the connection member of the first element comprises an arm extending radially outward from the first end and includes an opening sized to receive a hook extending from the proximal portion. In another embodiment, the connection member of the second element comprises an arm extending radially outward from the first end and includes an opening sized to receive the hooks extending from the proximal portion of the first segment and the distal end of the second segment.

The foregoing and other objects, aspects, features and advantages of the present invention will be more fully understood from the following description and embodiments when read together with the accompanying drawings.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention.

FIG. 1A is a side view of one embodiment of a prostatic stent according to the invention.

FIG. 1B shows an enlarged perspective view of a representative section of the coil segment labeled B in FIG. 1A.

FIG. 1C shows an enlarged cross-sectional view taken along a line C—C in FIG. 1B.

FIG. 1D shows an enlarged view of the proximal end of the stent in FIG. 1A.

FIG. 4A is a schematic view of the prostatic stent connected to the delivery system depicted in FIG. 3.

FIG. 4B is a schematic view of the prostatic stent connected to the delivery system depicted in FIG. 3 and in a configuration for insertion into the urethra of the patient.

DESCRIPTION

Figure 2:
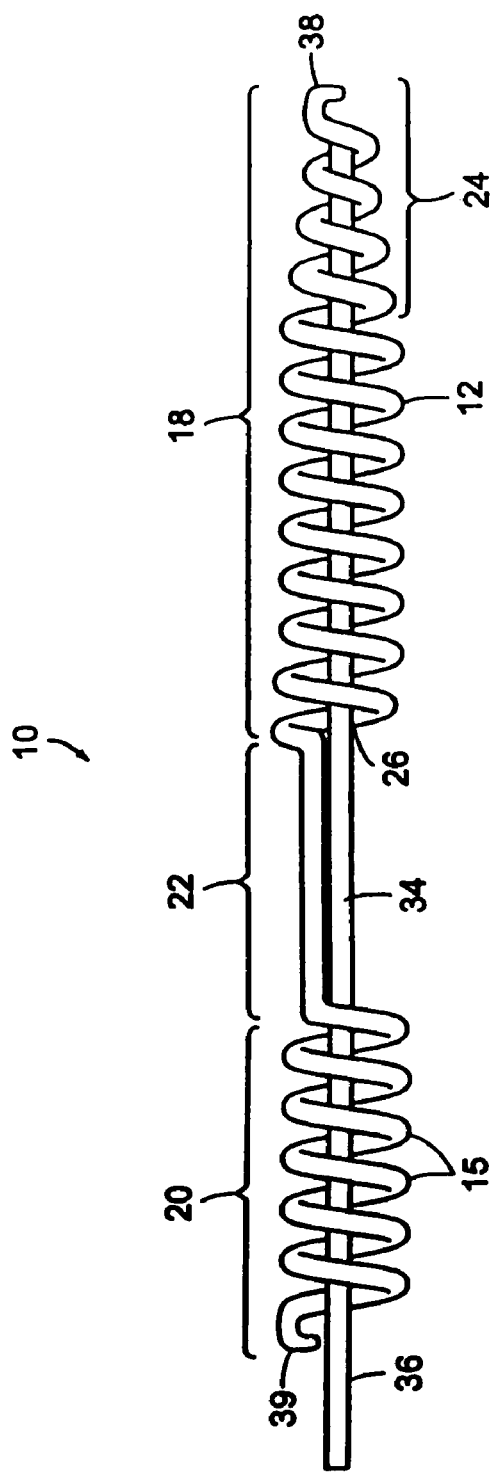
FIG. 2 is a side view of a prostatic stent including a frusto-conical proximal tip.

The invention generally relates to relieving urinary retention. The invention provides devices and methods for assisting urinary release in a male patient suffering from bladder outlet obstruction while allowing normal functioning of the patient's external sphincter such that the patient has control over bladder voiding.

Some men, especially men over fifty years of age, experience urinary retention caused by an enlarged prostate. The prostate is a chestnut shaped organ that surrounds the urethra in a man's urinary system. When it becomes enlarged due to disease or changes in male hormone production, the prostate can constrict the urethra resulting in bladder outlet obstruction. The medical condition described above is generally referred to as benign prostatic hyperplasia (BPH). In addition to the obstruction caused by the enlarged prostate, blood clots or other debris collecting in the constricted urethra may further obstruct the urethra of a patient suffering from BPH. One of the objects of the invention is to maintain an open passageway clear of debris from the patient's bladder through the urethra while preserving the patient's normal control of voiding function by allowing the external sphincter to open and close normally and under patient control. A further object of the invention is to permit practical removal of the device by the patient, thereby avoiding the cost and inconvenience of returning to a medical practitioner's office following the conclusion of treatment of the urological disorder.

Referring to FIG. 1A, the prostatic stent 10, in accordance with an embodiment of the invention, comprises an elongate coil segment 12 extending substantially longitudinally and including two distinct layers. As depicted in FIGS. 1B and 1C, the coil segment 12 of prostatic stent 10 comprises an inner core 13 surrounded by an outer coating 14 of thickness W. In other embodiments (not shown), the outer coating 14 may only partially surround the inner core 13. The inner core 13 is made from one or more biocompatible materials such as a polyimid. The outer coating 14 is made of a material which can be absorbed into the body and which provides the rigid support for the stent 10 when implanted in the male urinary system. The outer coating 14 is preferably a polyglycolic acid, polylactic acid, or a polymer blend, for example. In general, any biocompatible and bio-absorbable material(s) capable of providing rigid support for the stent 10 can be used for the outer coating 14.

The coil segment 12 is wound to form a plurality of windings 15 spaced from each other along some of the length of the coil segment 12. The plurality of windings 15 form a first coil (or prostatic segment) 18 and a second coil (or bulbar segment) 20. The windings 15 along the prostatic segment 18 defines a first lumen 21a and the windings 15 along the bulbar segment 20 defines a second lumen 21b. The first lumen 21a and second lumen 21b extend longitudinally along the prostatic stent 10 to allow fluid(s), such as urine, to pass therethrough. The prostatic segment 18 and the bulbar segment 20 are coupled together by a substantially unwound section along the coil segment 12 that defines a connecting segment 22.

The windings 15 of those sections of the stent 10 are sufficiently flexible to conform to the shape of the urethra for ease of insertion while sufficiently rigid to maintain an open passageway through the urethra when placed in the male urinary system. The segments 18, 20 can have cross-sectional shapes that are circular or can have other cross-sectional shapes, such as elliptical or even rectangular, square, or triangular, for example. In the embodiment of FIG. 1A, the prostatic stent 10 includes a proximal tip 24 extending proximally from the prostatic segment 18. An end view of the prostatic stent 10 at the proximal tip 24 is depicted in FIG. 1D. The connecting segment 22 connects to the prostatic segment 18 at a distal end 26. The proximal tip 24 can be either of constant diameter as shown in FIG. 1A, or a tapered diameter as shown in FIG. 2, yielding a conical or frusto-conical shape providing an atraumatic tip for ease of insertion into the patient's urethra. The first lumen 21a extends through the prostatic segment 18 to the proximal tip 24 for fluidic communication with the bladder of the patient.

A removal segment 34 continues from the proximal tip 24, through the prostatic segment 18, along the connecting segment 22, and through the bulbar segment 20, such that a distal portion 36 of the removal segment 34 may extend outside the penis when the prostatic stent 10 is implanted in the male urinary system. In one embodiment, the prostatic stent 10 is manufactured by heat setting the inner core 13 comprising the polyimid material in the desired coiled configuration defining the prostatic and bulbar segments 18, 20 about a mandrel at approximately 240 degrees Celsius for approximately two hours.

The prostatic and bulbar segments 18, 20 may also include hooks 38, 39. The hooks 38, 39 are positioned such that the prostatic stent 10 may be connected to a delivery device 40 (see FIG. 3) used to wind the prostatic stent 10 to a smaller width for delivery into the body of the patient. In the embodiment shown in FIG. 1A, the hooks 38, 39 are positioned such that they extend lengthwise beyond the prostatic and bulbar segments 18, 20, respectively. The hooks 38, 39 need not be positioned as shown in FIG. 1A to allow the coil segment 12 to connect to the delivery device 40 as other hook positions are possible.

When the prostatic stent 10 is properly positioned within a male patient's urinary system, the proximal tip 24 is located within the bladder near the bladder opening, the prostatic segment 18 is located substantially within the prostatic urethra (the section of the urethra that is surrounded by the patient's prostate) with the distal end 26 of the prostatic segment 18 terminating just prior to the proximal side of the patient's external sphincter, and the bulbar segment 20 is located on the distal side of the external sphincter. The connecting segment 22 is sized to extend through the external sphincter to attach the bulbar segment 20 to the prostatic segment 18 while not interfering with the normal operation of the external sphincter. The connecting segment 22 in the embodiment shown in FIG. 1A is substantially an uncoiled portion of coil segment 12. In alternative embodiments, the connecting segment 22 may be a helical coil with a diameter smaller than that of prostatic and bulbar segments 18, 20. Each of the ends of the connecting segment 22 smoothly transitions to the respective prostatic and bulbar segments 18, 20, so as to form no rough discontinuities or edges that would promote the formation of blood clots or collection of other bodily material.

To retain proper positioning of the prostatic stent 10 when positioned within the patient's body and to inhibit movement, the prostatic and bulbar segments 18, 20 have a greater diameter than connecting segment 22. When properly positioned within the patient's body, the prostatic stent 10 is located substantially within the patient's prostatic urethra with the prostatic segment 18 located within the bladder opening and the bulbar segment 20 located on the proximal side of the patient's external sphincter, so as not to interfere with the normal operation of the external sphincter. The greater diameter of the prostatic and bulbar segments 18, 20 is sized such that prostatic and bulbar segments 18, 20 are in contact with and exert a compressive force on the patient's urethral wall, thereby anchoring the prostatic stent 10 within the patient's urinary system and preventing the migration of the prostatic stent 10. The greater diameter of the prostatic segment 18 prevents the distal migration of the prostatic stent 10 (down and out of the bladder opening). Similarly, the greater diameter of the bulbar segment 20 prevents the proximal migration of the prostatic stent 10 (up into the bladder of the patient). In one disclosed embodiment, the diameter of the prostatic and bulbar segments 18, 20 is about 40 French.

FIG. 1C shows an enlarged cross-sectional view of the coil segment 12 taken along a line C—C in FIG. 1B. A dimension labeled W defines the wall thickness of the segment. Thickness W may be varied to effect the rate of absorption of the outer coating 14. The material composition and heat treatment of the outer coating 14 may also be selected to vary the rate of absorption or degradation.

The prostatic stent 10 may also include the removal segment 34. The removal segment 34 continues from the proximal tip 24 and is threaded back through the prostatic segment 18, the connecting segment 22, and the bulbar segment 20. The distal portion of the removal segment terminates outside of the patient's body when the prostatic stent 10 is placed within the urinary system of the patient for removal from the patient's body by a medical professional or patient. After the outer coating 14 is substantially absorbed into the patient's body, the stent 10, comprising now substantially the inner core 13, is sufficiently compliant to permit easy removal. For removal, the patient or medical professional pulls on the distal portion of the removal segment 36 along a longitudinal axis of the stent 10 to progressively unwind the windings 15 of the coil segment 12, enabling the stent 10 to assume a substantially linear configuration for complete withdraw from the patient's body.

One of the advantageous features of the prostatic stent 10 is its combination of radial strength and flexibility. The spaced windings 15 provide radial strength to the prostatic stent 10, while permitting the degree of flexibility necessary to conform to the patient's anatomy. In one embodiment the windings 15 are spaced such that a distance of about 1 millimeter exists between each adjacent winding. In other embodiments, where a greater amount of flexibility is desired, the windings 15 may be spaced at a greater distance, such as, for example, up to about 10 millimeters. Alternatively, if a greater amount of strength is required to maintain an open passageway through the patient's prostatic urethra, a medical professional may insert a prostatic stent 10 having windings 15 closely spaced, at a smaller distance. To maintain a desirable amount of flexibility to be able to conform to the patient's anatomy, the windings 15 may be spaced at a distance no less than about 0.5 millimeters.

Figure 3:
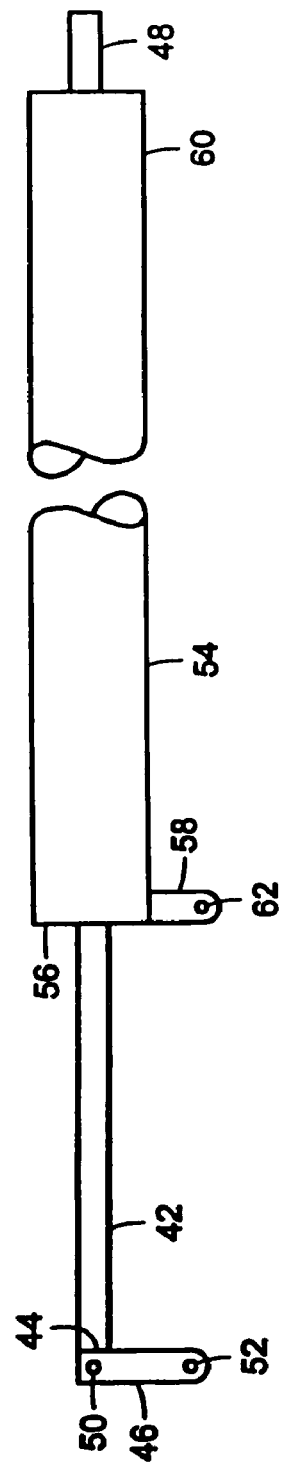
FIG. 3 is a side view of a one embodiment of a delivery system.

To wind, insert, position, and deploy the prostatic stent 10, a medical professional, such as, for example, a physician uses the delivery system 40 as shown in FIG. 3. The delivery system 40 can be made from a biocompatible material that is flexible enough to conform to the patient's body, but also rigid enough to advance the prostatic stent 10 through the patient's urinary system.

In the disclosed embodiment, the delivery system 40 includes a rotatable element 42 and has an outer diameter less than the smaller diameter of the prostatic and bulbar segments 18, 20 of the prostatic stent 10 so as to be insertable into the second lumen 21b of the prostatic stent 10. The rotatable element 42 includes a first end 44 having a connection arm 46 that extends radially outward from the first end 44, and a second end 48 that is accessible to the medical professional for positioning the prostatic stent 10 within the urinary system of the patient. The connection arm 46 may pivot about a hinge 50, which attaches the connection arm 46 to the rotatable element 42. The connection arm 46 includes an opening 52 that permits connection between the bulbar segment 20 of the prostatic stent 10 and the rotatable element 42. A stationary element 54 of the delivery system 40 includes a first end 56 having a connection arm 58 and a second end 60. The connection arm 58 extends radially outward from the first end 56 and includes an opening 62, which permits connection between the bulbar segment 18 of the prostatic stent 10 and the stationary element 54. In the disclosed embodiment, the stationary element 54 has an outer diameter larger than the diameter of prostatic and bulbar segments 18, 20 and includes a lumen sized to receive the rotatable element 42.

FIGS. 4A, 4B show one embodiment of the prostatic stent 10 having windings 15 of the coil segment 12 spaced apart at a large distance, L. Before the prostatic stent 10 is inserted into the patient's urinary system, the width of the winding of the coil segment 12 is reduced to allow the prostatic stent 10 to easily pass through the patient's urethra. One may reduce the width of the prostatic stent 10 to have a largest outer diameter that is in a range between about 16 French to about 18 French. The width of the prostatic stent 10 may be temporarily reduced by twisting or winding the proximal segment 18 about a longitudinal axis while restraining movement of the bulbar segment 20. Alternatively, twisting the bulbar segment 20 about the longitudinal axis while restraining the prostatic segment 18 may also reduce the width of the prostatic stent 10.

Alternatively, in another embodiment of a delivery system 40, the stationary element 54 may have an outer diameter less than or equal to the diameter of the rotatable element 42 such that the rotatable and stationary elements 42, 54 extend substantially parallel to each other when attached to the prostatic stent 10. In another embodiment, the stationary element 54 may be replaced with another rotatable element. In this embodiment, the two rotatable elements rotate in opposing directions. In a further embodiment, the delivery system 40 may also include a lumen extending through the rotatable element 42 from the first end 44 to the second end 48 to assist a medical professional with placing the prostatic stent 10 with the patient's urinary system.

Before inserting the prostatic stent 10 in the proper position within the patient's body, either a manufacturer or a medical professional (typically, the manufacturer) uses the stationary and rotatable elements to reduce the outer diameter or width of the prostatic stent 10. By reducing the diameter of the prostatic stent 10, possible injury or bruising to the urethra is substantially prevented during insertion and/or advancement of the prostatic stent 10 through the patient's urinary system. To connect the prostatic stent 10 with the delivery system 40, the manufacturer or medical professional attaches the bulbar segment 20 of the prostatic stent 10 to the first end 44 via the connection arm 46 of the rotatable element 42 and the prostatic segment 18 to the first end 56 via the connection arm 58 of the stationary element 54, as shown in FIG. 4A. In the disclosed embodiment, the connection arms 46, 58 have openings 52, 62 to permit connection to hooks 38, 39 extending from the prostatic and bulbar segments 18, 20 of the prostatic stent 10. Alternatively, the connection arms 46, 58 may be bent into hooks to permit connection with hooks 38, 39. Next, the manufacturer or the medical professional temporarily reduces the diameter of the prostatic stent 10 by twisting or ratcheting the rotatable element 42 that is attached to the prostatic segment 18 of the prostatic stent 10 while simultaneously holding the stationary element 54 that is connected to the bulbar segment 20 of the prostatic stent 10. By twisting the rotatable element 42 in a first direction as shown in FIG. 4B, the width of the prostatic stent 10 has decreased sufficiently to allow passage through the patient's urethra without significantly irritating or bruising the walls of the patient's urethra. As the width of the coil segment 12 is reduced, the length of the coil segment 12 consequently extends in longitudinal length. Upon being released from the delivery system, the coil segment 12 expands and the length of the coil segment 12 contracts until the prostatic stent 10 has returned to substantially its original dimensions.

Figure 5A:
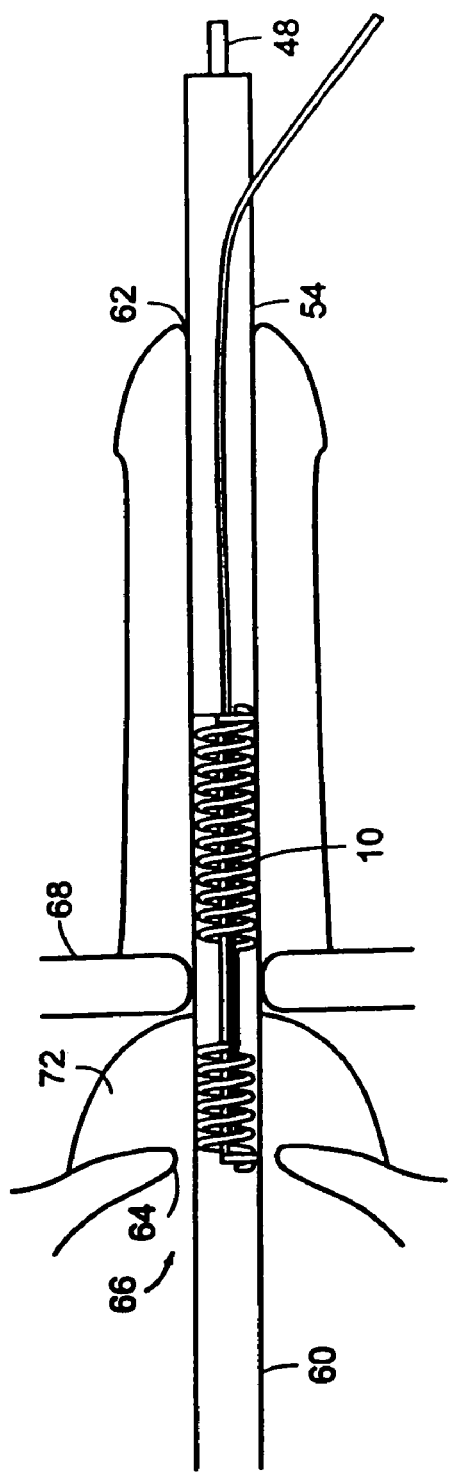
FIG. 5A is an expanded schematic view of a prostatic stent being inserted into the male patient's urinary system using the delivery system depicted in FIG. 3.

With the width of the prostatic stent 10 temporarily reduced, a medical professional inserts the prostatic stent 10 with attached delivery system into the meatus urinarius 62 of the patient, as shown in FIG. 5A. To further protect the patient's urethra from irritation, the medical professional may insert a sheath (not shown) into the patient's urethra 60 prior to inserting the prostatic stent 10 attached to the delivery system 40. The sheath is a smooth tubular member sized to receive the prostatic stent 10 and the delivery system 40. Alternatively, the prostatic stent 10 attached to the delivery system 40 may be inserted into the sheath prior to the medical professional inserting the sheath including the prostatic stent 10 and delivery system 40 into the patient's body.

Figure 5B:
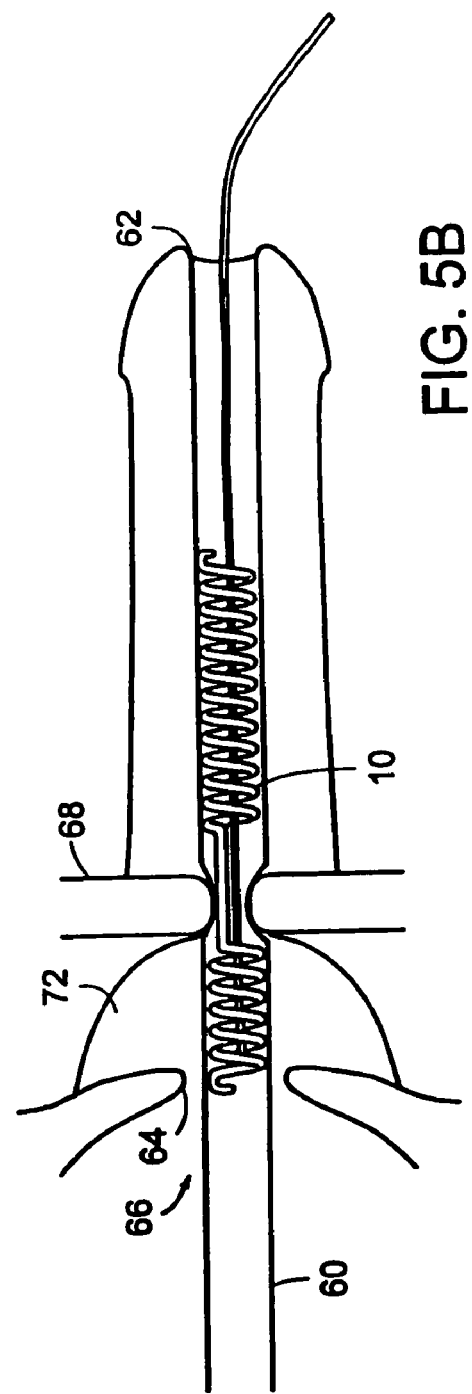
FIG. 5B is an expanded schematic view of a clinical application of a prostatic stent properly positioned in a male patient's urinary system.

With continued reference to FIG. 5A, the medical professional advances the prostatic stent 10 and the delivery system 40 through the patient's urinary system until the prostatic stent 10 is located substantially within the prostatic urethra with the prostatic segment 18 located near the opening of the patient's bladder 66 and the bulbar segment terminating prior to the proximal side of the patient's external sphincter 68 so as not to interfere with the normal operation of the external sphincter 68. After confirming proper placement of the prostatic stent 10 using, for example, radiographic techniques, the medical professional returns the prostatic stent 10 to its original or first width by rotating the rotatable element 42 in a second direction while restraining the stationary element 54 from moving. Once the prostatic stent 10 is returned to its original width, the prostatic and bulbar segments 18, 20 now with the restored, larger diameters on either side of the external sphincter 68, anchor the prostatic stent 10 within the proper position within the patient's urinary system as shown in FIG. 5B. The medical professional is then able to detach the rotatable element 42 from the prostatic segment 18 and the stationary element 54 from the bulbar segment 20 of the prostatic stent 10. With the connection arm 46 no longer attached to the prostatic stent 10, the connection arm 46 is able to pivot about hinge 50, thereby allowing the medical professional to remove the rotatable element 42 and the connection arm 46 from the prostatic stent 10 without dislodging the positioning of the prostatic stent 10 after placement. The detached rotatable element 42 and stationary element 54 are then removed from the patient's urinary system.

Figure 6A:
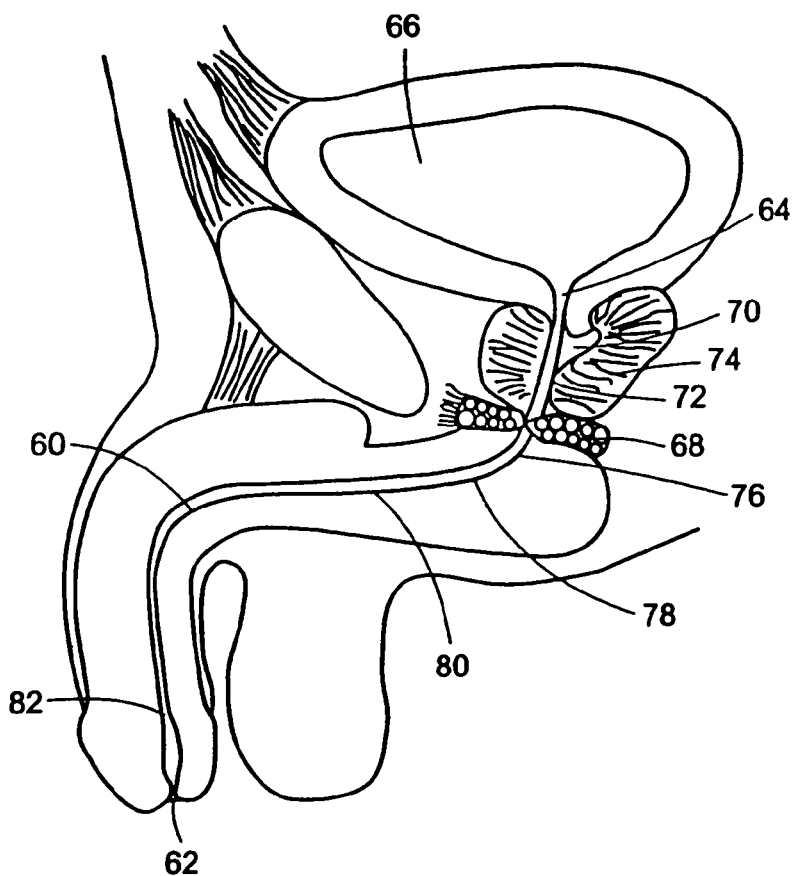
FIG. 6A is a view of a male patient's urinary system.
Figure 6B:
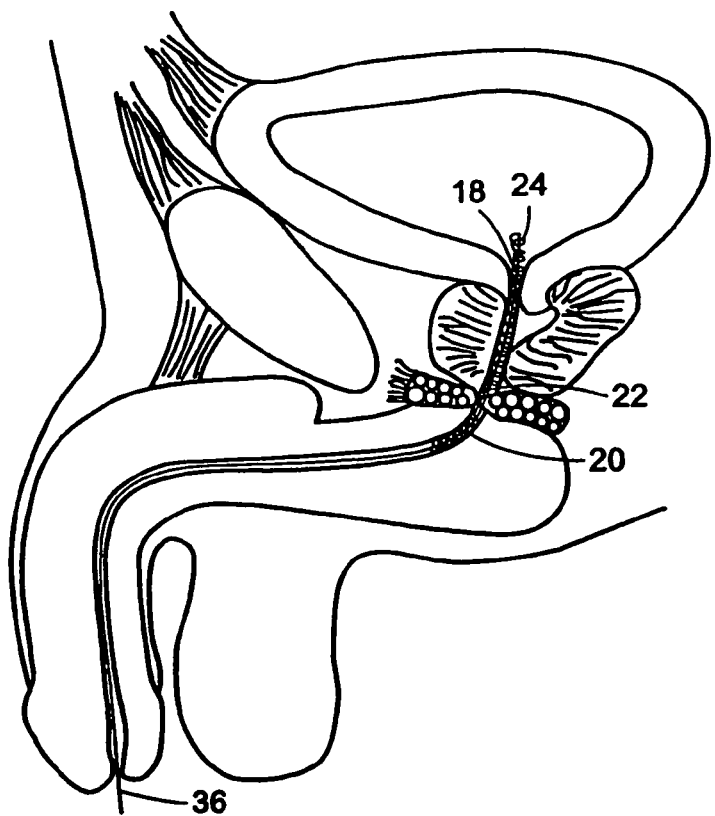
FIG. 6B is a view of the prostatic stent implanted in a male patient's urinary system.

Refer to FIG. 6A for a more detailed depiction of the male urinary system. The urethra extends upward from the meatus urinanus 62 as far as the neck 64 of the bladder 66. Above the external sphincter 68, the urethra comprises a super-collicular prostatic segment 70 and a sub-collicular prostatic segment 72 of the prostate 74. Below the external sphincter 68, the urethra comprises, toward the meatus urinarius 62, the membranous segments 76, the bulbar segment 78, the perineal segment 80, and the penile segment 82. The medical professional uses the delivery system 40 to advance the proximal tip 24 of the pro static stent 10 along the urethra 60, past the external sphincter 68, and into the bladder 66. The medical professional inserts the prostatic stent 10 connected with the delivery system 40 into the patient's urethra at the meatus urinarius 62. The medical professional then further advances the prostatic stent 10 such that the prostatic segment 18 is in the super-collicular prostatic section 70 of the urethra 60 surrounded by the prostate 74 with the bulbar segment 20 located on the distal side of the patient's external sphincter 68 along the bulbar segment 78 of the urethra 60. The prostatic stent 10 is properly positioned in the detailed depiction of the male urinary system as shown in FIG. 6B. At this point, the delivery system 40 extends from the bladder 66 through the urethra 60 and terminates at a location external to the patient's body. In another embodiment, (where the delivery system 40 includes a lumen extending through the rotatable element 42 from the first end 44 of the rotatable element to the second end 48), the medical professional looks for urine flowing from the second end of the rotatable element 48 of the delivery system 40 located external to the patient's body to confirm correct placement of the prostatic stent 10.

The positioned prostatic stent 10 maintains the patency of the patient's prostatic urethra, while simultaneously allowing the patient to control the opening and closing of the external sphincter 68. The positioned prostatic stent 10 has no parts or elements that communicate external to the patient's body during use, thereby reducing the high risk of infection associated with catheters. The radial strength provided by the coil segment 12 prevents the patient's prostatic urethra from collapsing due to the pressure created by the patient's enlarged prostate 68. The prostatic stent 10 is anchored in position by the prostatic and bulbar segments 18, 20 that inhibit migration of the prostatic stent 10.

Figure 7A:
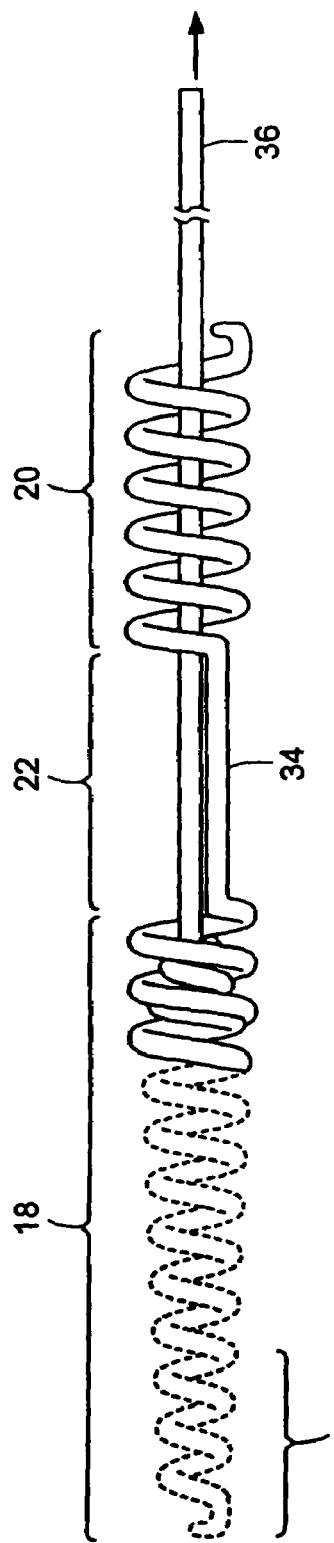
FIG. 7A is a side view of a prostatic stent properly being removed and uncoiled.
Figure 7B:
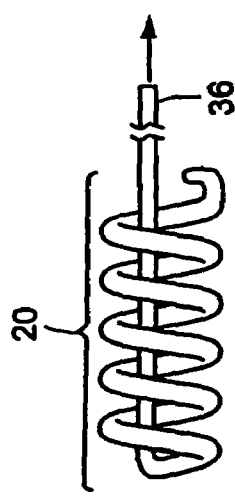
FIG. 7B is a side view of a prostatic stent being further removed and uncoiled.
Figure 7C:
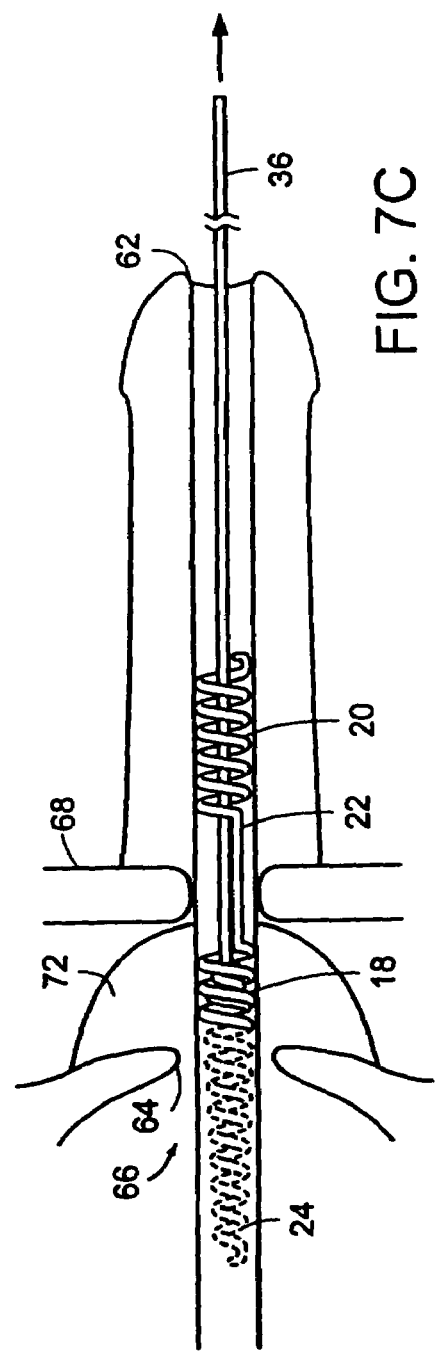
FIG. 7C is a schematic view of a prostatic stent being removed from the male patient's urinary system.

Referring to FIGS. 7A–7C the prostatic stent may be removed as follows. As all of the segments 18, 20, 22 and windings 15 of the prostatic stent 10 are formed from the single coil segment 12, the prostatic stent 10 may be removed by applying a tensile force along the removal segment 34, thereby unwinding the coil segment 12 and removing the prostatic stent 10. At the end of a prescribed time period, the patient can remove the prostatic stent 10 by pulling on the distal portion of the removal segment 36 extending back from the proximal tip 24, threaded through the prostatic and bulbar segments 18, 20 and extending through the penile segment 82 and through the meatus urinarius 62. When the outer coating 14 of the coil segment 12 is substantially absorbed, the structurally integrity of the prostatic stent 10 is sufficiently attenuated to permit removal of the prostatic stent 10 transurethrally by the patient. As the distal portion of the removal segment 36 is continuously pulled, the proximal tip 24 of the prostatic segment 18 first unwinds and the remainder of the stent 10 progressively unwinds until uncoiling and removal of the prostatic stent 10 is achieved. As this invention is designed for indwelling within a lumen for a prescribed time period of minimal duration, incorporation of the stent within the urethra due to tissue ingrowth is not a concern.

Variations, modifications, and other implementations of what is described herein will occur to those of ordinary skill in the art without departing from the spirit and the scope of the invention. Accordingly, the invention is not to be limited to only the preceding illustrative description.

What is claimed is:

1. A urethral stent for use within a patient, the stent comprising:
   a first anchoring segment disposed on the proximal side of the external sphincter when the stent is placed within the body of the patient;
   a second anchoring segment disposed on the distal side of the external sphincter when the stent is placed within the body of the patient;
   a connecting segment extending through the external sphincter when the stent is placed within the body of the patient, the connecting segment disposed between and coupling together the first anchoring segment and the second anchoring segment; and
   a removal segment continuing from the first anchoring segment and including a distal portion disposed outside the body of the patient when the first anchoring segment is placed within the body of the patient.

2. The medical device of claim 1 wherein at least one of the first anchoring segment and the second anchoring segment comprises a coil having a plurality of windings.

3. The medical device of claim 1 wherein the first anchoring segment comprises a coil having a plurality of windings and the second anchoring segment comprises a coil having a plurality of windings and the windings of the first anchoring segment and the second anchoring segment are sized and configured to progressively uncoil upon application of a continuous tensile force to the removal segment.

4. The medical device of claim 3 wherein the removal segment continues from the first anchoring segment, through the first anchoring segment coil, along the connecting segment, and through the second anchoring segment coil.

5. The medical device of claim 4, wherein the removal segment extends through the second anchoring segment and extends outside the body of the patient when the device is placed within the body of the patient.

6. The medical device of claim 1 wherein at least one of the first anchoring segment and the second anchoring segment defines a lumen.

7. The medical device of claim 1 wherein at least one of the first anchoring segment, the second anchoring segment, and the connecting segment further comprises an inner core and an outer coating covering at least a portion of the inner core.

8. The medical device of claim 1 wherein a proximal end of the first anchoring segment comprises an atraumatic tip.

9. The medical device of claim 1 wherein at least one of the first anchoring segment and the second anchoring segment comprises a cross-sectional shape selected from the group consisting of circular, elliptical, rectangular, square, and triangular.

10. The medical device of claim 1 wherein the removal segment is attached to a proximal end of the first anchoring segment.

11. A medical device for use within a urethra of a patient, the device comprising:
   a stent comprising:
      a coil including a plurality of windings and disposed on the proximal side of the external sphincter when the device is placed within the urethra of the patient;
      an anchoring segment disposed on the distal side of the external sphincter when the device is placed within the urethra of the patient;
      a connecting segment extending through the external sphincter when the device is placed within the urethra of the patient, the connecting segment disposed between and coupling together the coil and the anchoring segment; and
      a removal segment continuing from the coil and including a distal portion disposed outside the body of the patient when the coil is placed within the urethra of the patient.

12. The medical device of claim 11 wherein the anchoring segment comprises a second coil having a plurality of windings.

13. The medical device of claim 12 wherein the windings of the coil and the anchoring segment second coil are sized and configured to progressively uncoil upon application of a continuous tensile force to the removal segment.

14. The medical device of claim 11 wherein the coil defines a lumen.

15. The medical device of claim 11 wherein at least one of the coil and the anchoring segment comprises a cross-sectional shape selected from the group consisting of circular, elliptical, rectangular, square, and triangular.

16. A urethral stent, comprising:
   a first coil including a plurality of windings defining a first lumen, the first coil disposed on the proximal side of the external sphincter when the stent is placed within a urethra of a patient;
   a second coil including a plurality of windings defining a second lumen, the second coil disposed on the distal side of the external sphincter when the stent is placed within the urethra of the patient;
   a connecting segment extending through the external sphincter when the stent is placed within the urethra of the patient, the connecting segment connecting the first and second coils; and
   a removal segment continuing from the first coil and including a distal portion disposed outside the body of the patient when the rest of the stent is placed within the urethra of the patient.

17. The urethral stent of claim 16 wherein the removal segment continues from a proximal end of the first coil.

* * * * *